United States Patent
Lane et al.

(10) Patent No.: US 8,999,365 B2
(45) Date of Patent: Apr. 7, 2015

(54) PREVENTION OF BACTERIAL CONTAMINATION

(75) Inventors: Jonathan Lane, Surrey (GB); Olof Torgny Sjodin, Surrey (GB)

(73) Assignee: Sinclair Pharmaceuticals Limited, Godalming (GB)

( * ) Notice: Subject to any disclaimer, the term of this patent is extended or adjusted under 35 U.S.C. 154(b) by 940 days.

(21) Appl. No.: 11/814,925

(22) PCT Filed: Feb. 1, 2006

(86) PCT No.: PCT/GB2006/000335
§ 371 (c)(1), (2), (4) Date: Jan. 3, 2008

(87) PCT Pub. No.: WO2006/082393
PCT Pub. Date: Aug. 10, 2006

(65) Prior Publication Data
US 2008/0152688 A1    Jun. 26, 2008

(30) Foreign Application Priority Data
Feb. 1, 2005    (GB) .................................. 0502046.6

(51) Int. Cl.
| | | |
|---|---|---|
| A61F 2/00 | (2006.01) | |
| A01N 61/00 | (2006.01) | |
| A01N 43/84 | (2006.01) | |
| A01N 33/08 | (2006.01) | |
| A61K 8/49 | (2006.01) | |
| A61Q 11/00 | (2006.01) | |
| A61Q 17/00 | (2006.01) | |

(52) U.S. Cl.
CPC ............... *A01N 43/84* (2013.01); *A01N 33/08* (2013.01); *A61K 8/49* (2013.01); *A61Q 11/00* (2013.01); *A61Q 17/005* (2013.01)

(58) Field of Classification Search
CPC ....... A61K 8/49; A61Q 17/005; A01N 49/00; A01N 43/40; A01N 33/08; A01N 43/84
USPC .......................................... 424/422, 423, 405
See application file for complete search history.

(56) References Cited

U.S. PATENT DOCUMENTS

| 4,438,011 | A | 3/1984 | Howes |
| 4,894,221 | A | 1/1990 | Hernestam et al. |
| 5,500,206 | A | 3/1996 | Charbonneau |
| 6,235,269 | B1 | 5/2001 | Witt et al. |
| 2008/0064711 | A1 | 3/2008 | Friedman |
| 2010/0215704 | A1 | 8/2010 | Sjodin |

FOREIGN PATENT DOCUMENTS

| EP | 0 038 785 | | 10/1981 | |
| EP | 0398426 | A1 | 11/1990 | |
| GB | 1 428 748 | | 3/1976 | |
| RU | 2057130 | | 3/1996 | |
| RU | 2223746 | | 2/2004 | |
| SU | 536220 | A | 11/1976 | |
| WO | WO/87/05779 | | 10/1987 | |
| WO | WO 93/15195 | | 8/1993 | |
| WO | WO00/16624 | * | 3/2000 | ............ A01N 41/02 |
| WO | WO-01/01958 | A1 | 1/2001 | |
| WO | WO 02/02061 | | 1/2002 | |
| WO | WO/02/074274 | | 9/2002 | |
| WO | WO/03/105785 | | 12/2003 | |
| WO | WO 2004/078782 | | 9/2004 | |
| WO | WO/2004/100884 | | 11/2004 | |
| WO | WO 2006/082393 | | 8/2006 | |
| WO | WO 2007/000924 | | 1/2007 | |
| WO | WO 2007/010294 | | 1/2007 | |
| WO | WO 2007/060413 | | 5/2007 | |
| WO | WO 2008/019187 | | 2/2008 | |
| WO | WO 2008/139170 | | 11/2008 | |

OTHER PUBLICATIONS

J.C. Hase, et al, 6-Month Use of 0.2% Delmopinol Hydrochloride in Comparison with 0.2% Chlorhexidine Digluconate and Placebo, 25 J. Clin. Periodontol. 841, 842 (1998).*

J. Rundegren, et al, Effect of Delmopinol on the Cohesion of Glucan-containing Plaque Formed by *Streptococcus mutans* in a Flow Cell System, 71 J. Dent. Res. 1792, 1794-95 (Nov. 1992).*

Stefan Burgemeister, et al, Bactericidal Effect of Delmopinol on Attached and Planktonic *Streptococcus sanguinis* Cells, 109 Eur. J. Oral Sci. 425 (2001).*

J.P. Simmer & A.G. Fincham, Molecular Mechanisms of Dental Enamel Formation, 6 Crit. Rev. Oral Bio. Med. 84 (1995).*

Baehni et al., "Anti-plaque agents in the prevention of biofilm-associated oral diseases," *Oral Diseases* 9 11 , 23-29 2003.

(Continued)

*Primary Examiner* — Misook Yu
*Assistant Examiner* — Kauser M Akhoon
(74) *Attorney, Agent, or Firm* — Saliwanchik, Lloyd & Eisenschenk

(57) ABSTRACT

A compound of formula I: wherein $R_1$ is a straight or branched alkyl group containing 8 to 16 carbon atoms at the 2- or 3-position of the morpholino ring, and $R_2$ is a straight or branched alkyl group containing 2 to 10 carbon atoms, substituted with a hydroxy group except in the alpha-position, the sum of the carbon atoms in the groups $R_1$ and $R_2$ being at least 10 and preferably 10 to 20, is used to prevent biofilm formation on a surface. The compounds are particularly useful as coatings or treatments for medical devices, including stents, catheters and wire guides.

(I)

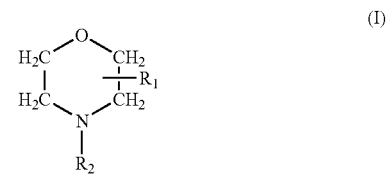

24 Claims, No Drawings

(56) References Cited

OTHER PUBLICATIONS

Burgemeister et al., "Bactercidal effect of delmopinol on attached and planktonic *Streptococcus sanguinis* cells," *European Journal of Oral Sciences*, 109 (6), 425-427 (2001).
Marsh, P.D.,"Dental plaque as a microbial biofilm," *Caries Research* 38(3) 204-211 (2004).
International Search Report from corresponding PCT/GB2006/000335 dated May 18, 2006.
International Preliminary Report on Patentability from corresponding PCT/GB2006/000335 dated May 25, 2007.
Elworthy et al., Antimicrobial properties of delmopinol against oral bacteria. *Lett. Appl. Microbiol.* 20: 191-4 (1995).
Database Registry Chemical Library, UkrOrgSynthesis, Jan. 20, 2009, XP002511572, retrieved from STN accession No. RN1094544-90-7, abstract.
Database Registry Chemical Catalog, Aurora Fine Chemicals, May 6, 2008, XP002511573, retrieved from STN accession No. RN1019574-04-9, abstract.
Database Registry Chemical Library, Ambinter, Nov. 15, 2007, XP002511574, retrieved from STN accession No. RN953748-38-4, abstract.
Merriam-Webster definition of "bandage", downloaded on Feb. 24, 2013, merriam-websters.com/dictionary/bandage.
Merriam-Webster definition of "clothing", downloaded on Feb. 24, 2013, merriam-webster.com/dictionary/clothing.
Merriam-Webster definition of "covering", downloaded on Feb. 24, 2013, merriam-webster.com/dictionnary/covering.
Liu, C. et al. "A New Small Molecule Specifically Inhibits the Cariogenic Bacterium *Streptococcus mutans* in Multispecies Biofilms" *Antimicrobial Agents & Chemo.*, 2011, 55(6):2679-2687.
Musk, D. et al. "Iron Salts perturb Biofilm Formation and Disrupt Existing Biofilms of *Pseudomonas aeruginosa*" *Chem. & Biol.*, 2005, 12:789-796.
Percival, R.S. et al. "The effect of cocoa polyphenols on the growth, metabolism, and biofilm formation by *Streptococcus mutans* and *Streptococcus sanguinis*" *Eur. J. Oral Sci.*, 2006, 114:343-348.
Office Action dated Aug. 31, 2012 in U.S. Appl. No. 12/669,716.
Office Action dated Mar. 25, 2013 in U.S. Appl. No. 12/669,716.
Office Action dated Oct. 9, 2013 in U.S. Appl. No. 12/669,716.

\* cited by examiner

_US 8,999,365 B2_

PREVENTION OF BACTERIAL CONTAMINATION

This application is a U.S. National Phase Application pursuant to 35 U.S.C. 371 of International Application No. PCT/GB06/00335, which was filed Feb. 1, 2006, claiming benefit of priority of Great Britain Patent Application No. 0502046.6, which was filed Feb. 1, 2005. The entire disclosure of each of the foregoing applications is incorporated herein by reference.

FIELD OF THE INVENTION

The present invention relates to the prevention of biofilm formation on medical devices and fluid-containing storage products.

BACKGROUND TO THE INVENTION

A biofilm may be described simply as "a community of microbes embedded in an organic polymer matrix, adhering to a surface" (Carpentier, 1993. J. Appl. Bacteriol. 75:499-511). All biofilms comprise three basic ingredients: microbes, a glycocalyx and a surface. If one of these components is removed, a biofilm will not develop.

A biofilm can be formed by a single bacterial species, but often biofilms consist of many species of bacteria together with fungi, algae, protozoa, debris and corrosion products. A biofilm can form on almost any surface exposed to bacteria and some amount of water.

The process of bacterial attachment to an available surface (living or abiotic) and the subsequent development of a biofilm is reviewed by W. Michael Dunne Jr, Clin Microbiol Rev. 2002 April; 15(2):155-66. Bacterial attachment is dictated by a number of variables, including the bacterial species, surface composition, environmental factors and essential gene products.

In simple terms, a biofilm forms when bacteria adhere to a surface in an aqueous environment and begin to excrete a slimy, glue-like substance which can anchor them to a range of materials—such as metals, plastics, soil particles, medical implant materials, and tissue.

Primary adhesion occurs through the chance meeting of a conditioned surface and a planktonic microorganism. As an oversimplification, primary adhesion between bacteria and abiotic surfaces is mediated by nonspecific (e.g. hydrophobic) interactions, whereas adhesion to living or devitalized tissue is accomplished through specific molecular (lectin, ligand, or adhesion) docking mechanisms. This stage is reversible and is dictated by physiochemical variables defining the interaction between the bacterial cell surface and the conditioned surface of interest.

After primary adhesion, an anchoring phase occurs, wherein loosely bound organisms consolidate adhesion by producing exopolysaccharides that complex with the surface, resulting in irreversible adhesion to the surface.

Once bacteria are irreversibly attached, biofilm maturation begins. The overall density and complexity of the biofilm increases, as surface-bound organisms actively replicate (and die) and extracellular components (generated by attached bacteria) interact with organic and inorganic molecules in the immediate environment to create the glycocalyx. Exopolysaccharides form the major component (excluding water) of the glycocalyx which, in most species, is predominantly anionic and traps nutrients while protecting the bacteria from environmental insults. In the case of infected biomedical implants, the glycocalyx may include host-derived inflammatory response proteins or matrix proteins such as complement, fibrinogen, and glycosaminoglycans attached to the implant.

The growth potential of a biofilm is limited by the availability of nutrients in the immediate environment, the perfusion of those nutrients to cells within the biofilm, and the removal of waste. An optimum hydrodynamic flow across the biofilm favours growth and perfusion rather than erosion of the outermost layers. Other factors that control biofilm maturation include internal pH, oxygen perfusion, carbon source, and osmolarity. At a critical mass, a dynamic equilibrium is reached at which the outermost layer of growth (farthest from the surface) generates planktonic organisms. These organisms are free to escape the biofilm and colonize other surfaces. Cells nearest the surface become quiescent or die due to a lack of nutrients or perfusion, decreased pH, $pO_2$, or an accumulation of toxic metabolic by-products.

Once anchored to a surface, biofilm microorganisms carry out a variety of detrimental or beneficial reactions (by human standards), depending on the surrounding environmental conditions. Microbial biofilms on surfaces cost billions of dollars yearly in equipment damage, product contamination, energy losses and medical infections. Conventional methods of killing bacteria (such as antibiotics and disinfection) are often ineffective with biofilm bacteria, partially due to the protective nature of the glycocalyx. The huge doses of antimicrobials required to rid systems of biofilm bacteria are environmentally undesirable (and may not be allowed by environmental regulations) and medically impractical (since the amount required to kill the biofilm bacteria would also have an adverse effect on the patient).

Although surfaces or surface coatings that retard bacterial adhesion have been described (e.g. Sheng et al, Diagn. Microbiol. Infect. Dis. 38:1-5), none have been developed that prevent it (p1-11, Lappin-Scott and Costerton, Microbial Biofilms 1995. Cambridge University Press). Accordingly, new strategies are required to manage biofilm formation.

SUMMARY OF THE INVENTION

The present invention is based on the realisation that delmopinol, and its derivatives, can be used to prevent or reduce biofilm formation or to ensure a non-pathogenic (non-viable) biofilm state. This can be used in industrial applications, including the prevention of biofilm formation on surgical devices or water storage or delivery devices.

According to a first aspect of the present invention, a compound having formula (I), or a salt thereof, is used for the prevention or reduction of biofilm formation on a surface, or to prevent or reduce viable microbial growth on a surface,

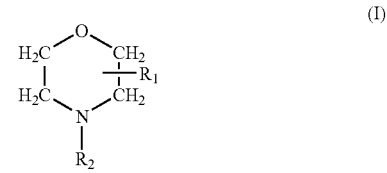

(I)

wherein $R_1$ is a straight or branched alkyl group containing 8 to 16 carbon atoms at the 2- or 3-position of the morpholino ring, and $R_2$ is a straight or branched alkyl group containing 2 to 10 carbon atoms, substituted with a hydroxy group except in the alpha-position, the sum of the carbon atoms in the groups $R_1$ and $R_2$ being at least 10 and preferably 10 to 20.

According to a second aspect of the present invention, there is the use of a compound as defined above for treating a surgical implement prior to surgery.

According to a third aspect of the present invention, there is a swab impregnated with a compound as defined above.

According to a fourth aspect of the present invention, there is a medical device coated with a compound as defined above.

According to a fifth aspect of the present invention, a filter, water delivery pipe or fluid storage tank is coated with a compound as defined above.

According to a sixth aspect of the invention, a container comprising a compound as defined above, is used for the treatment of a surface to prevent or reduce biofilm formation on the surface, or to prevent or reduce viable microbial growth on the surface.

According to a seventh aspect of the invention, a container comprises a plurality of individual sealed packages, each package comprising a unit dosage form of a compound as defined above, in liquid form.

DESCRIPTION OF THE INVENTION

The invention is based on the surprising discovery that delmopinol, and its derivatives, can prevent or reduce biofilm formation and/or can ensure that any bacterial biofilm is inactive, i.e. is in a non-viable state. The term "biofilm", as used herein, refers to the recognised meaning of the term in the art, i.e. a community of microbes and an associated glycocalyx, attached to a surface. A number of definitions exist in the art, each of which is within the scope of the current invention. For example, Carpentier (supra) describes a biofilm as "a community of microbes embedded in an organic polymer matrix, adhering to a surface"; Costerton (1999 Science 284:1318-1322) defines a biofilm as "a structured community of bacterial cells enclosed in a self-produced polymeric matrix and adherent to an inert or living surface."; Elder (1995 Eye 9:102-109) describes a biofilm in more cooperative terms as "a function consortium of microorganisms organised within an extensive exopolymer matrix".

The compounds for use in the present invention have the general formula (I) as shown above, wherein $R_1$ is a straight or branched alkyl group containing 8 to 16 carbon atoms at the 2- or 3-position of the morpholino ring, and $R_2$ is a straight or branched alkyl group containing 2 to 10 carbon atoms, substituted with a hydroxy group except in the alpha-position, the sum of the carbon atoms in the groups $R_1$ and $R_2$ being at least 10 and preferably 10 to 20. In a preferred embodiment, the compound is delmopinol, i.e. 3-(4-propyl-heptyl)-4-(2-hydroxyethyl) morpholine, a known compound.

The preparation of the compounds used in the invention is described in U.S. Pat. No. 4,894,221, the content of which is incorporated herein by reference.

In the following description reference is made to the "prevention or reduction of biofilm formation". However, the present invention also encompasses the treatment of surfaces to prevent or reduce the formation of "active" biofilms. Active biofilms are those characterised by viable microorganisms. Accordingly, reference to prevention of biofilm formation includes the prevention or reduction of the formation of viable microbial complexes or colonies or the reduction in the formation of such complexes or colonies. "Reduction" is measured by the comparison with an untreated surface.

The compounds may be used to treat any surface. Virtually any surface—animal, mineral, or vegetable (i.e., biotic or abiotic)—may be suitable for bacterial colonization and biofilm formation, including contact lenses, ship hulls, dairy and petroleum pipelines and all varieties of biomedical implants and transcutaneous devices; the compounds may therefore be used to prevent biofilm formation on any of these surfaces.

The compounds are of particular benefit in the prevention of biofilms on medical devices, e.g. surgical implants including artificial joints such as hips, orthopaedic hardware such as pins, plates and wires, artificial/prosthetic limbs, heart valves, stents, contact lenses and devices for delivering fluids, nutrients and medicines, or for the removal of fluids and waste, e.g. catheters. For the avoidance of doubt, the term "medical device", as used herein, includes devices and implants used in cosmetic procedures. The compounds may also be used to prevent biofilm formation on identification and information tags, or electronic chips, that are implanted into a subject.

The compound of the invention may also be used to treat surgical implements, e.g. surgical knives, saws, scalpels, forceps etc., or any other instrument used in an invasive surgical procedure.

The medical device may be an implant, i.e. a device that is inserted into the body of a subject. In a preferred embodiment, the device is a surgical implant that requires an incision to be made into the body to allow implantation. In a particularly preferred embodiment, the device to be treated is a dental implant, e.g. a tooth-retaining dental pin or screw. Alternatively, the medical device contacts the body but does not enter it, for example a prosthetic limb, plaster cast, contact lens or external hearing aid.

In the context of a contact lens, the compound of the invention may be impregnated onto the surface of the contact lens. Alternatively, in the context of hydrogel contact lenses, the compound may be impregnated into the hydrogel matrix. Alternatively, the compound may be present in the solution used to store or clean contact lenses.

The subject into (or onto) which the device is implanted (or contacted) may be human or animal, i.e. veterinary applications are within the scope of the invention.

The compound will usually be coated onto the surface or device to be treated. There are many ways in which compounds can be coated onto suitable substances, including spray coatings, irradiation and ultra violet curing. The technologies for coating medical devices with biomaterials are now advanced, and these technologies may be applied in the present invention. Accordingly, the present invention encompasses coated materials, in particular medical devices coated with the compound of formula I. Filter or water delivery pipes coated with the compound of formula I are also within the scope of the present invention, as are coated fluid storage or fluid delivery devices. The material to be coated may be metal, plastics, ceramic, polystyrene or glass. Preferably, the material to be coated is metal e.g. stainless steel.

The compound of the invention may be bound to the treated surface in a covalent or non-covalent attachment. If bound covalently, a linker molecule may be used to bind the compound to the surface. For example, polyethylene glycol (PEG) is a useful linker substrate that may be used in the present invention. Amination may also be used to provide an effective linker molecule.

Alternatively, the compound may be impregnated within a matrix, e.g. a polymer matrix. Conventional biocompatible polymer matrices may be used to retain the compound on the surface. For example, poly(organo)phophazene, hydrophilic hydrogels (e.g. 2-hydroxyethyl methacrylate; HEMA) or silicon-based coatings (e.g. fluorosilicone) are all used as conventional coatings on medical devices and may be used to retain a compound of the invention. A suitable method of coating is disclosed in US2005/0187611, the content of which is hereby incorporated by reference.

In a preferred embodiment, a medical device is contacted with a compound of formula I prior to or during insertion into (or contact with) the subject into (or onto) which the implant is to be deposited. More preferably, the device is rinsed in the compound prior to or during contact with the subject. Most preferably, rinsing occurs immediately prior to contact with the subject, with subsequent drying to coat the compound onto the device.

A preferred embodiment of the invention comprises an amount of the compound of formula I suitable for a single application to the medical device, or other surface, within a container. Preferably, the internal surfaces of the container, it's internal environment and contents (e.g. delmopinol) are aseptic, i.e. sterile and substantially free from pathogens, and therefore suitable for use in a medical (or cosmetic) operation such as surgery. More preferably, the external surfaces are also sterile. Any container suitable for holding a liquid may be used, it is preferred that the container can be sealed. A preferred container is a sachet, or pouch, that can be sealed aseptically on production and cut or torn open when required. Preferably, the sachet is made from a flexible plastic or metal material; suitable sachets are known in the art. Other suitable containers include bottles, jars and tubes of any material, preferably glass or plastic. In a preferred embodiment, the container is a holder for the storage or cleaning of a contact lens. The size of the container (and therefore the pre-determined dosage of compound stored within) suitable for different applications will be apparent to one skilled in the art, for example a hip implant will require a larger amount of delmopinol than a (standard) catheter. It is preferred that each container is "single-use", i.e. once it has been opened and the contents used, it is disposed of, irrespective of whether all of the contents have been used. This has the advantage of minimising any potential contamination.

The compound of the invention may be present in the container in any suitable concentration. Typically, the compound is present in a concentration of from 0.01% (w/v) to 10% (w/v), preferably from 0.1% (w/v) to 5% (w/v) and most preferably from 1% (w/v) to 3% (w/v) e.g. 2% (w/v). The compound will typically be present in a water solution, although any other suitable solvent may be used, including alcohol.

The compounds of formula I may be impregnated onto a material that is used to contact the surface onto which biofilm formation is to be prevented. The material may be woven or non-woven. A woven material will typically be used to wipe the surface; non-limiting examples of suitable woven materials include a swab, cloth, wipe or mop. The woven material may comprise natural (eg cotton) or synthetic fibres (eg nylon), or a combination of both. In a preferred embodiment, the impregnated material is an aseptic/sterile "single-use" material, suitable for use in a medical environment e.g. a bandage. Most preferably, the material is supplied in a container as described above; the container may comprise the impregnated material only, or the impregnated material and an excess of the compound suitable for rinsing the surface (in addition to, or instead of, contacting it with the impregnated material).

The compounds of formula I are also useful in other industrial applications where a fluid, e.g. water, is brought into contact with a surface. In a preferred embodiment, the compounds are used to prevent biofilm formation in water or fluid delivery or storage systems, including water purification or transportation systems, including water pipes and water storage tanks.

In another preferred embodiment, the surface itself is coated or impregnated with a compound according to the invention. This embodiment is particularly suitable for surfaces that will remain in situ for a prolonged period of time, for example medical devices and the water or fluid delivery systems described above.

The compounds may be brought into contact with the surface to be treated in a conventional way. For example, the compounds may be prepared in solution and the solution brought into contact with the surface.

The compounds may be used to rinse or wipe the surface, as described above. In a further preferred embodiment, the compound is sprayed onto the surface. In this embodiment, the compound may be prepared in an aerosol canister, atomiser spray bottle or other similar device, suitable for producing a droplet-based mist containing the compound. This is an effective method of contacting large surfaces with the compound. This is also particularly effective for contacting awkwardly shaped surfaces, or delicate surfaces such as contact lenses.

The compounds may be delivered in any suitable form that achieves the desired effect. The compounds may be included in a controlled release formulation or stored within a device that permits the controlled release of the compound. A controlled release formulation may be used in combination with any other embodiment described herein, for example a controlled release formulation may be impregnated into a surface, or delivered using a spray.

The compound of the invention may be used in any of its salt forms. In particular, the compound may be in its acid salt form (e.g. delmopinol HCL) or in its low solubility in water solutions. The compound will therefore be retained at the surface of the treated device, even after rinsing.

The amount effective to prevent biofilm formation will be readily apparent to the skilled person and may be determined based on the surface to be treated.

The invention is further described in the following non-limiting example.

EXAMPLE

Test Surfaces

The following test materials were included in the study:
stainless surgical steel 316 (for e.g. heart valves)
titanium (for e.g. hip implants)

The different materials were obtained as discs with an approximate diameter of 30 mm and a thickness of 1 mm. These discs were then mounted in the bottom of Petri dishes Test Compound Delmopinol hydrochloride, was dissolved in water of UHQ grade to a concentration of 20 mg/mL (2% w/v). The solution was stored in the dark at room temperature until use.

Treatment of Test Surfaces with Delmopinol

Procedure A: The test surfaces were treated with 2 mL of the 2% aqueous solution of delmopinol HCl and left unstirred for 15 minutes at room temperature. All delmopinol solution was removed with a pipette. The wells were then thoroughly rinsed three times with 4 mL of a potassium phosphate buffer, 10 mM, pH 7.2. Since the pKa of delmopinol is 7.1, a substantial part of the compound will be converted to its base, which has a very low solubility in water solutions and will thus remain at the surface and not be completely washed off during the rinsing procedure.

Procedure B: The test surfaces were treated with 2 mL of the 2% aqueous solution of delmopinol HCl and left overnight to dry.

Microorganisms

A fresh bacterial strain of Staphylococcus epidermidis was isolated from skin and stored in milk powder at −80° C. The day before experimental use, bacteria were transferred to blood agar and incubated in an atmosphere of 95% $H_2$ and 5% $CO_2$ at 37° C. overnight. Colony-forming units were collected from the blood agar and suspended in 10 mM potassium phosphate buffer, pH 7.2, to an optical density at 600 nm of 0.4, corresponding to approximately $10^8$ cells/mL.

The bacterial viability of the bacterial suspension, indicated by the vitality percentages, was assessed by fluorescence microscopy using the Live/Dead Bacterial Viability method Molecular Probes, Inc. Eugene, Oreg., USA) according to the instructions of the manufacturer. Thus, SYTO 9 (1.5 μL) and propidium iodide (1.5 μL) were mixed with 1 mL of 10 mM phosphate buffer, pH 7.2. Aliquots of 10 μL were added to 10 μL cell suspension and analysed at 1000× for green/LIVE and red/DEAD cells in the fluorescence microscope (Leitz Aristoplan microscope equipped with a halogen lamp and a 470-490 nm excitation filter).

In all cases the viability of cell cultures was more than 95%.

Adhesion Assay Method

Four mL of the bacterial suspension was added on top of coated and non-coated test surfaces mounted in Petri dishes. The cells were allowed to adhere for 60 min at 37° C. Non-adherent cells were removed by rinsing the surfaces three times with 4 mL of the buffer solution. All liquid on the surface was removed and adherent bacteria were visualized using the stains SYTO 9 and propidium iodide as described above. A 10 μL-aliquot of the mixture was added to the surface and analysed after 10 min incubation in the dark. Microscopic images of adherent cells were analysed from 10 fields of each disc. The images were captured with a digital camera connected to the microscope and used for averaging the number of attached cells in separate fields. The number of attached cells, as well as the percentage vital cells, was estimated using the mathematical program MATLAB.

Detachment Assay Method

Adherent cell populations were prepared on delmopinol-coated surfaces as described above. In order to test whether cells were removed from the surface with delmopinol, the surfaces were rinsed three times with 2% delmopinol in water followed by analysis with fluorescence microscopy.

I. The Effect of Delmopinol-Coating on Adhesion

Triplicate cultures of the bacterial strains were used and the mean values of the different runs are presented. The total (viable and non-viable) numbers of attached cells are presented in Table 1.

Comparison of adhesion to surfaces coated or not coated with delmopinol. Figures represent the number of cells per $mm^2$ on given surfaces pre-treated or not pre-treated with a 2% solution of delmopinol HCl.

TABLE 1

| Exp. | Stainless steel | | Titanium | |
| --- | --- | --- | --- | --- |
| No. | Non-coated | Coated | Non-coated | Coated |
| I | 250 | 739 | 377 | 415 |
| II | 227 | 241 | 1070 | 110 |
| III | 332 | 273 | 703 | 95 |
| Mean | 270 | 418 | 717 | 207 |

II. The Effect of Delmopinol-Coating on Bacterial Viability

Triplicate cultures of the bacterial strains were treated as described above and the mean values of the different runs are presented in Table 2.

Comparison of bacterial viability on surfaces coated or not coated with delmopinol. Figures represent percentage viable cells on given test surfaces.

TABLE 2

| Exp. | Stainless steel | | Titanium | |
| --- | --- | --- | --- | --- |
| No. | Non-coated | Coated | Non-coated | Coated |
| I | 83 | 10 | 69 | 5 |
| II | 28 | 0 | 43 | 11 |
| III | 63 | 17 | 67 | 11 |
| Mean | 58 | 9 | 60 | 9 |

III. Growth of Adherent Bacteria on Treated and Non-Treated Surfaces

The ability of bacteria to grow on coated and non-coated surfaces was determined by adding 4 mL of Tryptic Yeast Extract medium to each well and incubating at 37° C. The results indicate that growth on solid surfaces is inhibited by delmopinol-coating (Table 3).

TABLE 3

| | Stainless steel | | Titanium | |
| --- | --- | --- | --- | --- |
| Cell culture IV | Non-coated | Coated | Non-coated | Coated |
| Growth after 1 day | yes | no | yes | no |
| Growth after 5 days | | no | | no |

In conclusion, the delmopinol-coated surfaces showed a significant reduction in the viability of adherent cells and the delmopinol significantly inhibited growth of surface-associated bacteria.

The invention claimed is:

1. A method for the inhibition of biofilm on a surface of a surgical implant, said method comprising coating or impregnating the surface of the implant prior to surgery with a material comprising a compound of formula (I) or a salt thereof:

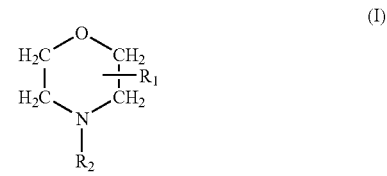

(I)

wherein $R_1$ is a straight or branched alkyl group containing 8 to 16 carbon atoms at the 2- or 3-position of the morpholino ring, and $R_2$ is a straight or branched alkyl group containing 2 to 10 carbon atoms, substituted with a hydroxy group except in the alpha-position, the sum of the carbon atoms in the groups $R_1$ and $R_2$ being at least 10 and preferably 10 to 20; wherein the implant is a transcutaneous device, catheter, stent, guide wire, or orthopedic prosthetic; and wherein the surface of the implant comprises metal.

2. The method of claim 1, wherein the material is woven.

3. A method for treating a biomedical device prior to use, comprising contacting the surface of the device with a compound of formula (I):

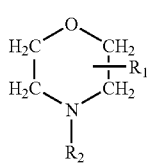

wherein $R_1$ is a straight or branched alkyl group containing 8 to 16 carbon atoms at the 2- or 3-position of the morpholino ring, and $R_2$ is a straight or branched alkyl group containing 2 to 10 carbon atoms, substituted with a hydroxy group except in the alpha-position, the sum of the carbon atoms in the groups $R_1$ and $R_2$ being at least 10 and preferably 10 to 20; wherein the device is a transcutaneous device, catheter, stent, guide wire, or orthopedic prosthetic; and wherein the surface of the device comprises metal.

4. The method of claim 3, wherein the surface of the device is contacted with the compound of formula (I) prior to or during insertion into, or contact with, a subject.

5. The method of claim 3, wherein the surface of the device is rinsed with the compound of formula (I).

6. The method of claim 4, wherein the surface of the device is rinsed with the compound of formula (I).

7. The method of claim 3, further comprising inserting the device into a human or animal subject after said contacting.

8. The method of claim 3, further comprising inserting the device into a human or animal subject transcutaneously after said contacting.

9. The method of 1, wherein the implant requires an incision to be made into the body to allow implantation of the implant.

10. The method of claim 3, wherein the device is not a device that remains in situ in a subject for a prolonged period of time.

11. The method of claim 1, wherein the compound is delmopinol.

12. The method of claim 1, wherein the compound is delmopinol hydrochloride.

13. The method of claim 1, wherein the implant is the transcutaneous device.

14. The method of claim 1, wherein the implant is the catheter.

15. The method of claim 1, wherein the implant is the stent.

16. The method of claim 1, wherein the implant is the guide wire.

17. The method of claim 1, wherein the implant is the orthopedic prosthetic.

18. The method of claim 3, wherein the compound is delmopinol.

19. The method of claim 3, wherein the compound is delmopinol hydrochloride.

20. The method of claim 3, wherein the device is the transcutaneous device.

21. The method of claim 3, wherein the device is the catheter.

22. The method of claim 3, wherein the device is the stent.

23. The method of claim 3, wherein the device is the guide wire.

24. The method of claim 3, wherein the device is the orthopedic prosthetic.

* * * * *